United States Patent
Baumann et al.

(10) Patent No.: US 9,554,761 B2
(45) Date of Patent: Jan. 31, 2017

(54) C-ARM MOUNTING APPARATUS AND X-RAY IMAGING DEVICE WITH CAGE GUIDE

(71) Applicants: Berthold Baumann, Kastl (DE); Wolfgang Neuber, Pressath (DE); Matthias Schirbl, Freihung (DE)

(72) Inventors: Berthold Baumann, Kastl (DE); Wolfgang Neuber, Pressath (DE); Matthias Schirbl, Freihung (DE)

(73) Assignee: Siemens Aktiengesellschaft, München (DE)

( * ) Notice: Subject to any disclaimer, the term of this patent is extended or adjusted under 35 U.S.C. 154(b) by 123 days.

(21) Appl. No.: 14/332,800

(22) Filed: Jul. 16, 2014

(65) Prior Publication Data
US 2015/0023470 A1    Jan. 22, 2015

(30) Foreign Application Priority Data
Jul. 17, 2013   (DE) ........................ 10 2013 213 996

(51) Int. Cl.
*H05G 1/02*    (2006.01)
*A61B 6/00*    (2006.01)
(Continued)

(52) U.S. Cl.
CPC ............ *A61B 6/4441* (2013.01); *F16C 33/36* (2013.01); *F16C 33/61* (2013.01); *A61B 6/4464* (2013.01); *F16C 29/005* (2013.01); *F16C 29/048* (2013.01)

(58) Field of Classification Search
CPC ......... G01N 23/04; A61B 6/032; A61B 6/035; A61B 6/44; A61B 6/4435; A61B 6/4441; H05G 1/02
(Continued)

(56) References Cited

U.S. PATENT DOCUMENTS 6,810,103 B1 * 10/2004  Tybinkowski ......... A61B 6/032
                                                      250/363.04
7,434,996 B2 * 10/2008  Wang ................... A61B 6/4441
                                                      378/193
(Continued)

FOREIGN PATENT DOCUMENTS

CN    201377516 Y    1/2010
CN    102641132 A    8/2012
(Continued)

OTHER PUBLICATIONS

German Office Action dated Mar. 10, 2014 in corresponding German Patent Application No. DE 10 2013 213 996.9 with English translation.
(Continued)

*Primary Examiner* — Jurie Yun
(74) *Attorney, Agent, or Firm* — Lempia Summerfield Katz LLC

(57) ABSTRACT

A C-arm mounting apparatus for an x-ray imaging device includes a C-arm, a C-arm holding unit, and at least one cage guide unit. The at least one cage guide unit is moveably arranged between the C-arm and the C-arm holding unit. The C-arm is moveably mounted on the C-arm holding unit. The at least one cage guide unit includes a plurality of rolling bodies and at least one rolling body cage. The small overlap between the C-arm and the C-arm holding unit may facilitate greater rotations about an isocenter. An x-ray imaging device includes a C-arm mounting apparatus.

20 Claims, 5 Drawing Sheets

(51) Int. Cl.
  *F16C 33/36*   (2006.01)
  *F16C 33/61*   (2006.01)
  F16C 29/00   (2006.01)
  F16C 29/04   (2006.01)

(58) Field of Classification Search
  USPC .................................. 378/62, 193, 197, 198
  See application file for complete search history.

(56) References Cited

U.S. PATENT DOCUMENTS

| | | |
|---|---|---|
| 2002/0118793 A1 | 8/2002 | Horbaschek |
| 2002/0150314 A1 | 10/2002 | De Vries |
| 2006/0039537 A1* | 2/2006 | Strobel .................. A61B 6/032 |
| | | 378/197 |
| 2007/0036273 A1 | 2/2007 | Noda |
| 2008/0175354 A1 | 7/2008 | Wang et al. |

FOREIGN PATENT DOCUMENTS

| | | |
|---|---|---|
| DE | 10109754 | 9/2002 |
| DE | 202011107140 | 5/2012 |
| DE | 102011004228 A1 | 8/2012 |

OTHER PUBLICATIONS

Chinese office Action for related Chinese Application No. 201410330651.7 dated Aug. 11, 2016, with English Translation.

* cited by examiner

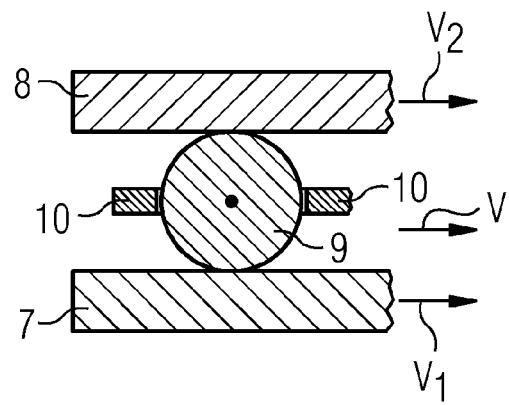
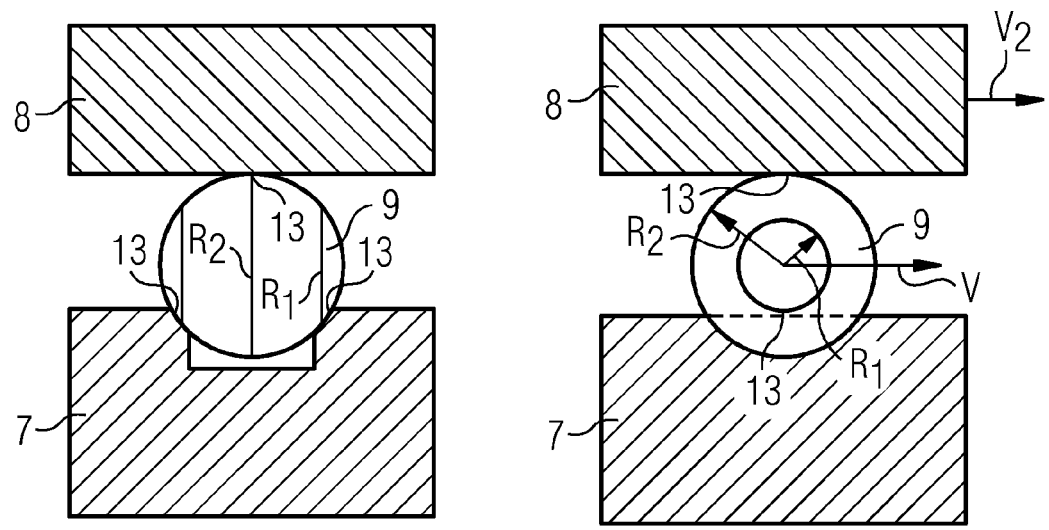

FIG 3
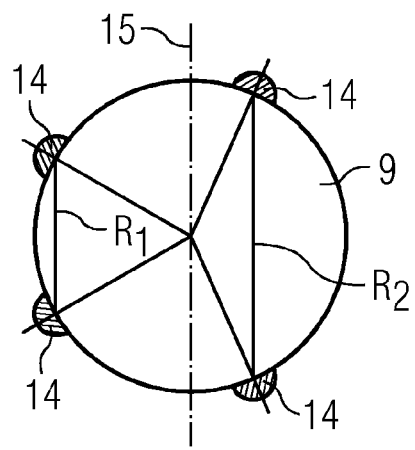
FIG 4
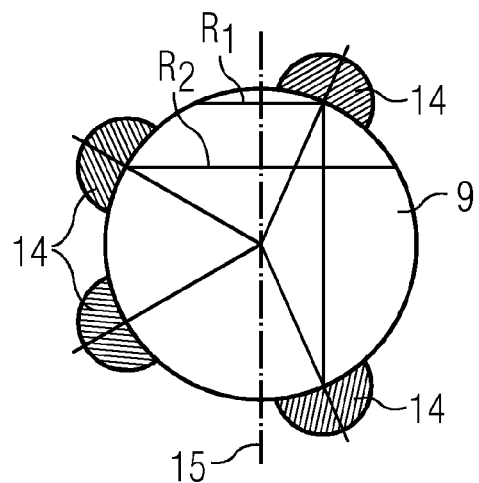
FIG 5
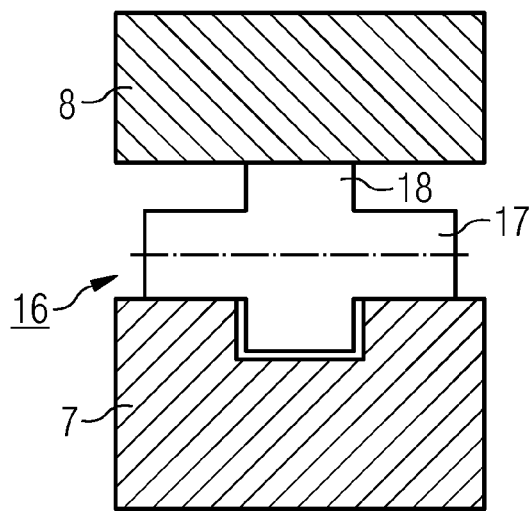
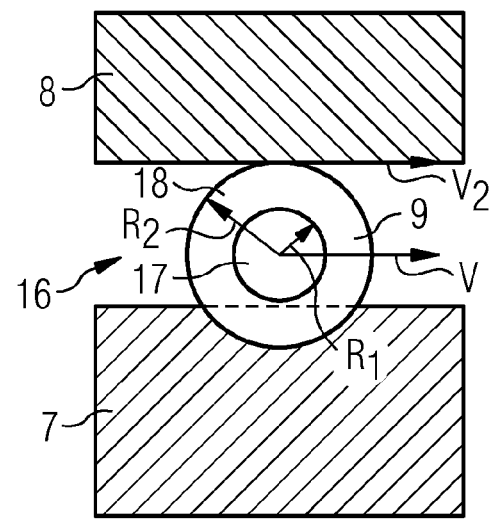

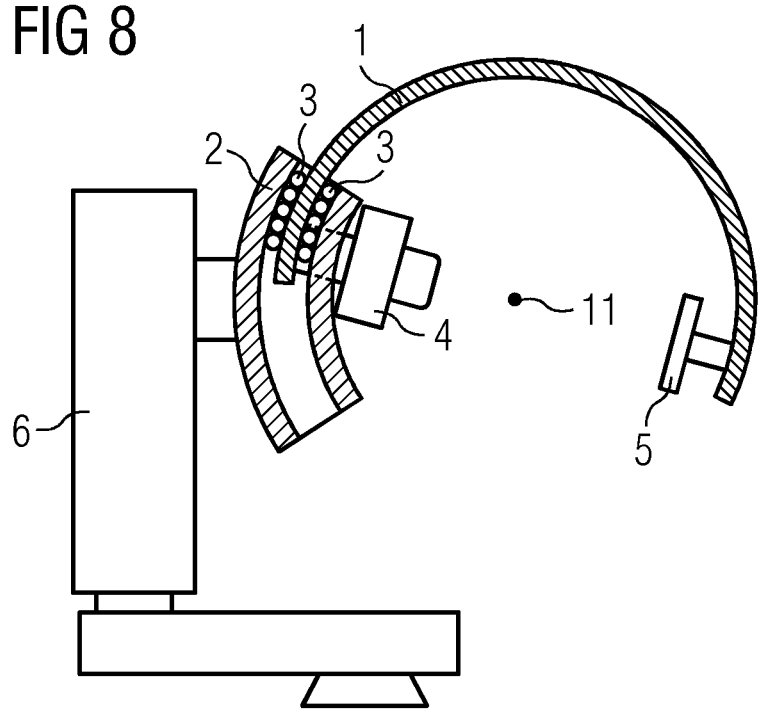
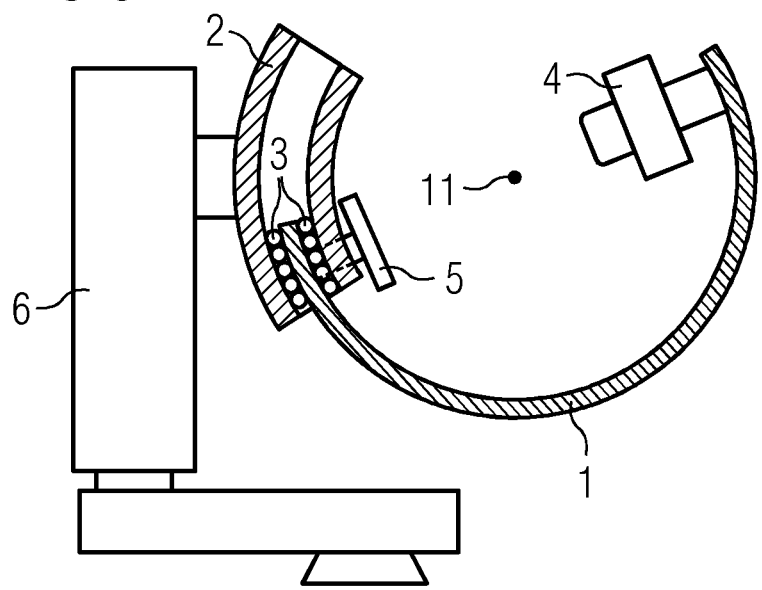

C-ARM MOUNTING APPARATUS AND X-RAY IMAGING DEVICE WITH CAGE GUIDE

RELATED APPLICATIONS

This application claims the benefit of German Patent Application No. DE 102013213996.9, filed Jul. 17, 2013. The entire contents of the priority document are hereby incorporated herein by reference.

TECHNICAL FIELD

The present teachings relate generally to apparatuses for displaceably (e.g., moveably) mounting a C-arm in a C-arm holding unit with the aid of a cage guide. In some embodiments, the present teachings further relate to x-ray imaging devices including a C-arm that is displaceable in the C-arm holding unit.

BACKGROUND

X-ray imaging devices are used in fluoroscopy and radiography. In the x-ray imaging process, x-ray beams emitted by an x-ray emitter pass through an object before being incident on an x-ray detector, having been attenuated by the object. Some configurations of an x-ray imaging device include a C-arm.

In the laid-open document DE 101 097 54 A1, a C-arm x-ray device is described as a ceiling device. An x-ray emitter and an x-ray detector are fastened to the ends of the C-arm. The C-arm is mounted in a movable manner and may be rotated about a patient by a drive. In the process described in DE 101 097 54 A1, the C-arm moves along its own axis on guides that are embedded into the profile of the C-arm. The guide of the C-arm about the orbital axis has a plurality of rollers or roller pairs and guide wires that are made of steel and that have been introduced into the C-arm that is made of aluminum.

The utility model document DE 202011107140 U1 describes a roller guide of a C-arm. In the roller guide described therein, a stable mount is provided through complete overlap between a C-arm holder and the C-arm. As a result of the length of the C-arm, the length of the C-arm holder, and the guide of the C-arm, the described systems are restricted to a displacement range around the orbital axis of approximately 100°.

BACKGROUND AND SUMMARY

The scope of the present invention is defined solely by the appended claims, and is not affected to any degree by the statements within this summary.

The present embodiments may obviate one or more of the drawbacks or limitations in the related art. For example, in some embodiments, an apparatus for mounting a C-arm and an x-ray imaging device are provided that are able to carry out larger rotational movements of the C-arm about the orbital axis as compared to conventional approaches.

In accordance with the present teachings, a C-arm and a C-arm holding unit may be moveably mounted by a cage guide arranged therebetween. The phrase "cage guide" refers to a linear guide without a rolling body return section. A cage guide may include a guide rail pair and the rolling bodies arranged therebetween. The rolling bodies are held in a rolling body cage. In some embodiments, a transmission ratio between the rolling body cage and the C-arm of greater than 1:2 may be obtained by suitably configuring the rolling bodies and/or the C-arm holding unit and the C-arm whereupon the rolling bodies may roll.

A C-arm mounting apparatus for an x-ray imaging device in accordance with the present teachings includes a C-arm and a C-arm holding unit. The apparatus further includes at least one cage guide unit that is moveably arranged between the C-arm and the C-arm holding unit. The C-arm is moveably mounted on the at least one cage guide unit in the C-arm holding unit. The cage guide unit includes a plurality of rolling bodies and at least one rolling body cage. In accordance with the present teachings, greater displacement ranges of the C-arm may be achieved due to the small overlap between the C-arm and the C-arm holding unit.

In some embodiments, the C-arm holding unit and the C-arm may be configured such that the cage guide unit generates a transmission ratio of greater than 1:2, thereby facilitating passage of the C-arm over a great track around the orbital axis.

In other embodiments, the rolling bodies may be configured such that the cage guide unit generates a transmission ratio of greater than 1:2, thereby facilitating passage of the C-arm over a great track around the orbital axis.

In other embodiments, two guide wires may be formed on the C-arm holding unit and two guide wires may be formed on the C-arm. The rolling bodies are configured to roll on the guide wires, and the guide wires are configured with respect to one another such that the cage guide unit is configured to generate a transmission ratio of greater than 1:2.

The rolling bodies may have a first rolling radius and a second rolling radius. The first rolling radius defines the distance between the rolling body centers and points of support on the C-arm holding unit. The second rolling radius defines the distance between the rolling body centers and points of support on the C-arm. The first rolling radius is less than the second rolling radius.

In some embodiments, the cage guide unit may have an arcuate shape.

In some embodiments, the C-arm may be moveably arranged within the C-arm holding unit, and the C-arm may be mounted between at least two cage guide units.

In some embodiments, a first cage guide unit may be formed on a side of the C-arm facing an isocenter, and a second cage guide unit may be formed on a side of the C-arm facing away from the isocenter.

In some embodiments, the C-arm may be moveably mounted on the C-arm holding unit, and the C-arm may be mounted like a carriage between two cage guide units.

In some embodiments, the two cage guide units may be formed at the same distance from an isocenter.

The present teachings also provide an x-ray imaging device that includes an x-ray emitter, an x-ray detector, and a C-arm mounting apparatus of a type described herein.

BRIEF DESCRIPTION OF THE DRAWINGS

FIG. 1 shows a cross-sectional view of an example of a cage guide.

FIG. 2 shows a cross-sectional view of an example of a cage guide with a 1:4 transmission ratio based on an exemplary configuration of the points of support of the rolling bodies.

FIG. 3 shows a cross-sectional view of an example of a first cage guide with a 1:4 transmission ratio based on an exemplary configuration of the guide wires.

FIG. 4 shows a cross-sectional view of an example of a second cage guide with a 1:4 transmission ratio based on an exemplary configuration of the guide wires.

FIG. 5 shows a cross-sectional view of an example of a cage guide with a 1:4 transmission ratio based on an exemplary configuration of the rolling bodies.

FIG. 8 shows a cross-sectional view of an example of a C-arm x-ray device with a cage guide of the C-arm in an upper end position.

FIG. 9 shows a cross-sectional view of an example of a C-arm x-ray device with a cage guide of the C-arm in a lower end position.

DETAILED DESCRIPTION

Figure 6:
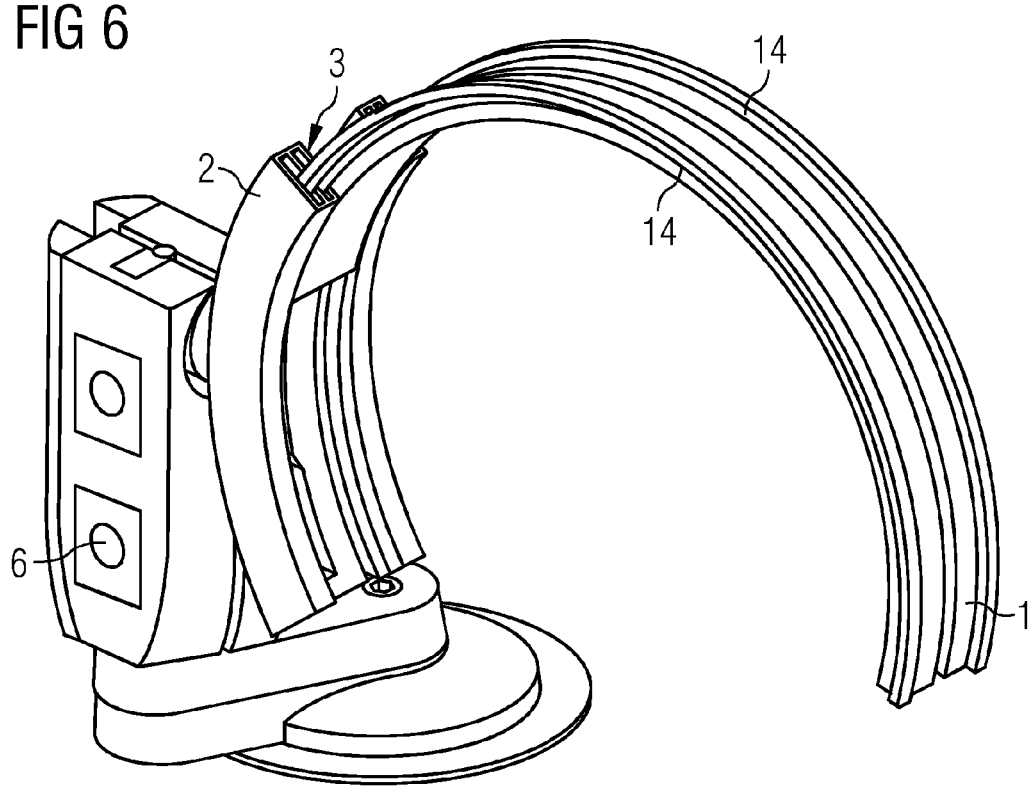
FIG. 6 shows a perspective view of an example of a C-arm mounting apparatus.

In order to increase the displacement range of a C-arm, the concept of a guide has been modified. For example, the C-arm is mounted by a cage guide unit rather than by using stationary rollers. As a result, the overlap between the C-arm and a C-arm holding unit may be reduced, and the displacement range may be increased.

In contrast to conventional designs, the rolling bodies (e.g., rollers, spheres, needles) of the guide are not mounted in the C-arm holding unit in a stationary manner. Rather, the cage guide unit (e.g., a rolling body cage with rolling bodies) is displaced in the C-arm holding unit according to the 1:2 cage guide principle. The transmitting mounting element is not assembled in a stationary manner but rather is automatically positioned in the C-arm holding unit. As further described below in reference to FIG. 1, a guide of the C-arm is thus provided. The guide may be telescopic.

FIG. 1 shows a cross-sectional view of an example of a cage guide with a first guide rail 7, a second guide rail 8, and a sphere 9. The sphere 9 is situated between the first guide rail 7 and the second guide rail 8 as a rolling body, and is held in a rolling body cage 10. The guide is based upon the principle of a rolling wheel.

The first guide rail 7 may be equated with a first velocity $v_1=0$. If the sphere 9 rolls, the center of the sphere 9 moves with a velocity v. Due to the position of the sphere 9 (e.g., the distance from the resting point of the sphere 9), the second guide rail 8 moves with a second velocity $v_2$ that has twice the magnitude of the velocity v, as indicated by the following equation: $v_2=2*v$.

By linking a plurality of spheres 9 at the sphere center points thereof by the rolling body cage 10, a cage may be constructed. Thus, the rolling body cage 10 moves at the velocity v, and the second guide rail 8 moves at twice the velocity v. Since the whole structure is observed during the same time interval, it may be determined that the second guide rail 8 always travels over twice the path length as compared to the rolling body cage 10. This 1:2 transmission ratio is independent of the type of rolling bodies employed (e.g., cylinder rollers, spheres, etc.).

In order to reduce the track of the cage guide in the C-arm holding unit, the transmission ratio between the cage guide unit and the C-arm may be increased. FIG. 2 depicts a transmission concept wherein a rolling body (e.g., a sphere) rolls over various radii.

In FIG. 2, the principle of a cage guide in accordance with the present teachings is exemplified for a transmission ratio of 1:4. The left-hand drawing shows an exemplary front view and the right-hand drawing shows an exemplary side view. A sphere 9 that comes into contact with first guide rail 7 and second guide rail 8 via points of support 13 is arranged between the first guide rail 7 and the second guide rail 8.

While the first guide rail 7 rolls on a smaller first rolling radius $R_1$ of the sphere 9, the second guide rail 8 rolls on a larger second rolling radius $R_2$ of the sphere 9. As a result, if a first guide rail 7 is stationary, the sphere 9 may move with a velocity v. Moreover, as a result of the 1:2 ratio of the radii, the second guide rail 8 may move with a second velocity $v_2$ having four times the magnitude, as shown in the following equation: $v_2=4*v$.

As a result, a 1:4 transmission is created. By rolling the sphere 9 over different rolling radii $R_1$ and $R_2$, almost any transmission ratio may be set. Since the production of guide rails with a stepped configuration may be complicated, suitably configured guide wires may also be used in place of the first guide rail 7 and the second guide rail 8.

Each of FIGS. 3 and 4 shows a cross-sectional view of a sphere 9 being guided between guide wires 14 while the sphere 9 rotates about its rotational axis 15. Exemplary geometric dimensions for a 1:4 transmission ratio are depicted. As described above in reference to FIG. 2, the sphere 9 is rolled over two different rolling radii $R_1$ and $R_2$. The rolling of sphere 9 over two different rolling radii $R_1$ and $R_2$ is achieved via an angular shift of the guide wires 14 with respect to one another. In accordance with the present teachings, the guide wires 14 do not have a rectangular arrangement.

Although all four guide wires may be arranged in a rectangle in conventional sphere cage guides with sphere races, guide wires in accordance with the present teachings are arranged at different variable angles. As a result, the sphere 9 rolls over different rolling radii $R_1$ and $R_2$. The two rolling radii $R_1$ and $R_2$ have values of 9 mm and 18 mm, respectively. By rolling over two different rolling radii $R_1$ and $R_2$, an additional 1:2 transmission is created. Since the sphere 9 per se already has a transmission of 1:2 between the sphere center point (or cage) and the points on the second rolling radius $R_2$, an overall transmission of 1:4 between the cage and C-arm is achieved for a normal square arrangement of the guide wires 14 (cage principle).

The above-described configuration of the guide wires 14 may provide a simple and cost-effective solution to the problem of transmission. A cage guide is created by connecting the plurality of spheres 9, thereby providing direct positioning of the cage (e.g., friction between spheres 9 and guide wires 14) depending on the rolling radii $R_1$ and $R_2$ whereby the spheres 9 roll on the guide wires 14.

The difference in the cage guides in FIG. 3 and FIG. 4 merely lies in the embodiment of the guide wires.

In some embodiments, as shown in FIG. 5, a specialized configuration of a roller 16 may be used as the rolling body as an alternative to using an angle-offset configuration of guide wires. In such embodiments, any desired transmission may be created by redesigning conventional rollers. FIG. 5 shows an exemplary front view on the left-hand side, and an exemplary side view on the right-hand side. By way of example, the rollers 16 (only one being shown in FIG. 5 for the sake of simplicity) may include a first cylinder 17 and a second cylinder 18 that are offset from one another. While the smaller first cylinder 17 rolls on the first guide rail 7, the second larger cylinder 18 rolls on the second guide rail 8.

Therefore, the roller 16 (and, therefore, a cage connected thereto) moves at the velocity v on a stationary first guide rail 7. As a result, the second guide rail 8 moves with the n-times second velocity $v_2$ if the second rolling radius $R_2$ is n/2 times larger than the first rolling radius $R_1$. The second velocity may be expressed as follows: $v_2=n*v$.

Since the whole design is observed over a constant time interval, the second guide rail 8 always travels over n-times the path length of the roller 16, thereby resulting in a transmission between roller/cage and the second guide rail of 1:n.

As a result of configuring the rollers 16 with an offset and rolling the rollers 16 over different rolling radii $R_1$ and $R_2$, any desired transmission (1:n) may be created. By linking a plurality of rollers, a cage that may be used for guiding a C-arm about the orbital axis is created. As a result of rolling friction between the first guide rail 7, the second guide rail 8, and the rolling cage, a C-arm may be positioned without additional aids.

FIG. 5 shows an example of a cage guide with an exemplary configuration for a transmission of 1:4. The roller 16 includes first cylinders 17 and second cylinder 18 offset from one another. While the smaller first cylinder 17 rolls on the first guide rail 7 with the first rolling radius $R_1$, the larger second cylinder 18 rolls only on the second guide rail 8 with the rolling radius $R_2$ that has twice the size compared to the first rolling radius $R_1$. The rolling radius $R_2$ may be expressed as follows: $R_2=2*R_1$.

As a result, in the case of a stationary first guide rail 7, the roller 16 may move at the velocity v, and the second guide rail 8 may move at the second velocity $v_2$ with four times the magnitude. The second velocity $v_2$ may be expressed as follows: $v_2=4*v$.

Thus, a 1:4 transmission is created. By linking a plurality of rollers 16 on the roller axis, cage may be constructed. The cage moves at the velocity v and the second guide rail 8 moves at the second velocity $v_2$ (=4*v).

Since the whole structure is observed over the same time intervals, the guide rail 8 always travels over four times the path length compared to the cage, thereby resulting in a 1:4 transmission.

For embodiments that use a different first cylinder 17 and second cylinder 18, any desired transmission may be created by rolling the roller 16 over different rolling radii $R_1$ and $R_2$. As a result, direct positioning of the cage (e.g., friction between rollers and guide rails) may be achieved depending on the rolling radii $R_1$ and $R_2$ of the first cylinder 17 and second cylinder 18.

FIG. 6 depicts an exemplary embodiment of a C-arm guide and a mount in accordance with FIG. 5. A C-arm holding unit 2 is arranged on a stand 6. The C-arm 1 is moveably mounted in the C-arm holding unit 2 by the cage guide unit 3. For lateral fastening, guide wires 14 have been introduced into the C-arm 1 and into the C-arm holding unit 2 (not visible in FIG. 6). The guide wires serve as a race and a guide for the non-visible rollers of the cage guide unit 3 by introduced notches. The rollers include two cylinders offset from one another as shown in FIG. 5.

While the smaller first cylinder rolls on the C-arm holding unit 2, the larger second cylinder rolls on the C-arm 1. Therefore, the C-arm 1 always travels over four times the path length compared to the cage guide unit 3, thereby resulting in a transmission between the cage guide unit 3 and the C-arm 1 of 1:4.

Figure 7:
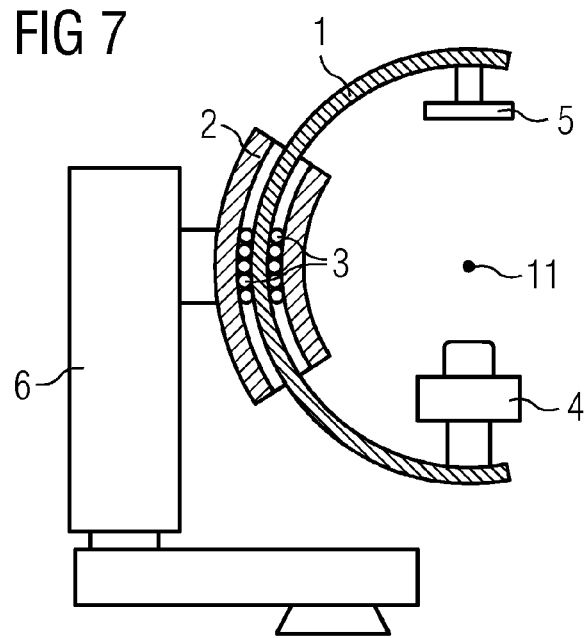
FIG. 7 shows a cross-sectional view of an example of a C-arm x-ray device with a cage guide of the C-arm in a home position.

If the principle described above in reference to FIGS. 1-5 is applied to a C-arm guide, a configuration as shown, for example, in FIGS. 7-9 may be obtained. Each of FIGS. 7-9 shows a cross-sectional view of a C-arm x-ray device with a cage guide of a C-arm 1. An x-ray emitter 4 and an x-ray detector 5 are fastened opposite to one another on the C-arm 1. The C-arm 1 is mounted within a C-arm holding unit 2. Four cage guide units 3 are arranged between the C-arm holding unit 2 and the C-arm 1. The C-arm is moveably arranged on the cage guide units around an isocenter 11. In FIGS. 7-9, only two of the four cage guide units 3 are visible.

Two cage guide units 3 are arranged within the C-arm 1, and two cage guide units 3 are arranged outside of the C-arm 1. As a result, the C-arm 1 may be guided in a stable manner. The rolling bodies (not shown) of the cage guide units 3 run on guide wires or guide rails (not shown).

In order to extend the displacement path of the C-arm 1, the C-arm holding unit 2 may also provide in a telescopic-type embodiment that includes a plurality of stacked cage guide units 3.

FIG. 7 shows the C-arm 1 in a home position. FIG. 8 shows the C-arm 1 in an upper end position, with the cage guide unit 3 being displaced up to the upper end of the C-arm holding unit 2. FIG. 9 shows the C-arm 1 in a lower end position, with the cage guide unit 3 being displaced down to the lower end of the C-arm holding unit 2.

Figure 10:
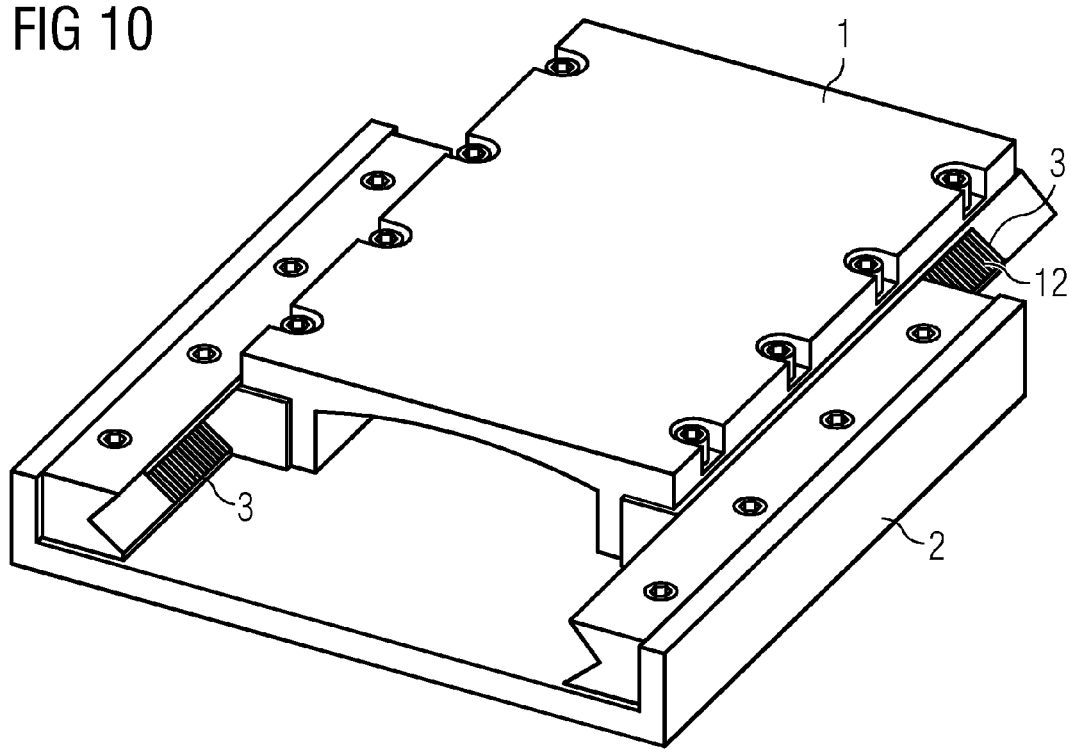
FIG. 10 shows an exemplary configuration of a cage guide as a linear carriage.

Other configurations of the cage guide unit 3 may be used. By way of example, FIG. 10 shows a linear carriage wherein the C-arm 1 (depicted as a section) is mounted in a moveably fitted manner between two cage guide units 3 that slide in the C-arm holding unit 2. The rolling bodies are embodied as needles 12 and form a V-shaped groove, wherein a complementarily shaped guide rail of the C-arm may be displaced.

For embodiments of C-arms 1 with a cage guide, larger displacement ranges may be achieved due to the smaller overlap between the C-arm 1 and the C-arm holding unit 2. Through application of a rolling wheel principle, driven positioning of the rolling body cage may be avoided. Instead, the C-arm 1 may be positioned relative to the C-arm holding unit 2. The rolling body cage automatically travels over half the path length of the C-arm 1 (e.g., friction between the rolling body and the guide rails and the 1:2 displacement resulting therefrom). Furthermore, a rigid and resilient mount of the C-arm 1 may be achieved by a relatively large number of supporting rolling bodies.

The present teachings are applicable in both floor-mounted (e.g., floor stand) and ceiling-mounted (e.g., second plane) x-ray devices. In addition, the present teachings may be used in connection with telescopic guides.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A C-arm mounting apparatus for an x-ray imaging device, the C-arm mounting apparatus comprising:
   a C-arm;
   a C-arm holding unit; and
   at least one cage guide unit;
      wherein the at least one cage guide unit is moveably arranged between the C-arm and the C-arm holding unit;
      wherein the C-arm is moveably mounted on the C-arm holding unit; and
      wherein the at least one cage guide unit comprises a plurality of rolling bodies, at least one rolling body cage, and a plurality of guide wires arranged at different variable angles.

2. The C-arm mounting apparatus of claim 1, wherein the at least one cage guide unit is configured to generate a transmission ratio of greater than 1:2.

3. The C-arm mounting apparatus of claim 2, wherein the transmission ratio is achieved through a configuration of the C-arm holding unit and the C-arm.

4. The C-arm mounting apparatus of claim 3, wherein each of the C-arm holding unit and the C-arm comprises two guide wires, wherein each rolling body of the plurality of rolling bodies is configured to roll on the guide wires of the C-arm holding unit and the guide wires of the C-arm, and wherein the transmission ratio is achieved through a configuration of the guide wires of the C-arm holding unit and the guide wires of the C-arm.

5. The C-arm mounting apparatus of claim 2, wherein the transmission ratio is achieved through a configuration of the plurality of rolling bodies.

6. The C-arm mounting apparatus of claim 5, wherein each rolling body of the plurality of rolling bodies comprises a first rolling radius and a second rolling radius, wherein the first rolling radius defines a distance between a rolling body center and a point of support on the C-arm holding unit, wherein the second rolling radius defines a distance between the rolling body center and a point of support on the C-arm, and wherein the first rolling radius is less than the second rolling radius.

7. The C-arm mounting apparatus of claim 2, wherein the transmission ratio is achieved through a configuration of the C-arm holding unit and the C-arm, and a configuration of the plurality of rolling bodies.

8. The C-arm mounting apparatus of claim 1, wherein the at least one cage guide unit comprises an arcuate shape.

9. The C-arm mounting apparatus of claim 1, further comprising at least one additional cage guide unit, wherein the C-arm is moveably arranged within the C-arm holding unit, and wherein the C-arm is mounted between the at least one cage guide unit and the at least one additional cage guide unit.

10. The C-arm mounting apparatus of claim 9, wherein one of the at least one cage guide unit and the at least one additional cage guide unit is formed on a side of the C-arm facing an isocenter, and wherein the other of the at least one cage guide unit and the at least one additional cage guide unit is formed on a side of the C-arm facing away from the isocenter.

11. The C-arm mounting apparatus of claim 1, further comprising at least one additional cage guide unit, wherein the C-arm is mounted on the C-arm holding unit in a carriage configuration between the at least one cage guide unit and the at least one additional cage guide unit.

12. The C-arm mounting apparatus of claim 11, wherein the at least one cage guide unit and the at least one additional cage guide unit are equidistant from an isocenter.

13. An x-ray imaging device, comprising:
   a C-arm mounting apparatus;
   an x-ray emitter; and
   an x-ray detector;
      wherein the C-arm mounting apparatus comprises:
         a C-arm;
         a C-arm holding unit; and
         at least one cage guide unit;
            wherein the at least one cage guide unit is moveably arranged between the C-arm and the C-arm holding unit;
            wherein the C-arm is moveably mounted on the C-arm holding unit; and
            wherein the at least one cage guide unit comprises
               a plurality of rolling bodies;
               at least one rolling body cage; and
               a plurality of guide wires arranged at different variable angles.

14. The x-ray imaging device of claim 13, wherein the at least one cage guide unit is configured to generate a transmission ratio of greater than 1:2.

15. The x-ray imaging device of claim 14, wherein each of the C-arm holding unit and the C-arm comprises two guide wires, wherein each rolling body of the plurality of rolling bodies is configured to roll on the guide wires of the C-arm holding unit and the guide wires of the C-arm, and wherein the transmission ratio is achieved through a configuration of the guide wires of the C-arm holding unit and the guide wires of the C-arm.

16. The x-ray imaging device of claim 13, wherein each rolling body of the plurality of rolling bodies comprises a first rolling radius and a second rolling radius, wherein the first rolling radius defines a distance between a rolling body center and a point of support on the C-arm holding unit, wherein the second rolling radius defines a distance between the rolling body center and a point of support on the C-arm, and wherein the first rolling radius is less than the second rolling radius.

17. The x-ray imaging device of claim 13, wherein the at least one cage guide unit comprises an arcuate shape.

18. The x-ray imaging device of claim 13, wherein the C-arm mounting apparatus further comprises at least one additional cage guide unit, wherein the C-arm is moveably arranged within the C-arm holding unit, and wherein the C-arm is mounted between the at least one cage guide unit and the at least one additional cage guide unit.

19. The x-ray imaging device of claim 18, wherein one of the at least one cage guide unit and the at least one additional cage guide unit is formed on a side of the C-arm facing an isocenter, and wherein the other of the at least one cage guide unit and the at least one additional cage guide unit is formed on a side of the C-arm facing away from the isocenter.

20. The x-ray imaging device of claim 18, wherein the at least one cage guide unit and the at least one additional cage guide unit are equidistant from an isocenter.

* * * * *